(12) United States Patent
Shanks et al.

(10) Patent No.: US 6,605,079 B2
(45) Date of Patent: Aug. 12, 2003

(54) METHOD FOR PERFORMING LIPOPLASTY USING EXTERNAL LASER RADIATION

(75) Inventors: Stephen C. Shanks, Mesa, AZ (US); Kevin B. Tucek, Gilbert, AZ (US); Rodrigo Neira, Cali (CO)

(73) Assignee: Erchonia Patent Holdings, LLC, Mesa, AZ (US)

( * ) Notice: Subject to any disclaimer, the term of this patent is extended or adjusted under 35 U.S.C. 154(b) by 0 days.

(21) Appl. No.: 10/028,169

(22) Filed: Oct. 19, 2001

(65) Prior Publication Data

US 2002/0123743 A1 Sep. 5, 2002

Related U.S. Application Data

(60) Provisional application No. 60/273,282, filed on Mar. 2, 2001.

(51) Int. Cl.$^7$ ............................................. A61B 18/20
(52) U.S. Cl. ........................... 606/2; 128/898; 604/542
(58) Field of Search ............................ 606/2; 604/542; 607/88, 89

(56) References Cited

U.S. PATENT DOCUMENTS

| | | | | |
|---|---|---|---|---|
| 4,886,491 A | * | 12/1989 | Parisi et al. | 604/22 |
| 5,472,416 A | * | 12/1995 | Blugerman et al. | 604/22 |
| 5,507,790 A | * | 4/1996 | Weiss | 600/2 |
| 5,649,924 A | | 7/1997 | Everett et al. | |
| 5,655,547 A | | 8/1997 | Karni | |
| 5,954,710 A | * | 9/1999 | Paolini et al. | 600/2 |
| 5,984,915 A | | 11/1999 | Loeb et al. | |
| 6,013,096 A | | 1/2000 | Tucek | |
| 6,106,516 A | | 8/2000 | Massengill | |
| 6,176,854 B1 | | 1/2001 | Cone | |
| 6,206,873 B1 | * | 3/2001 | Paolini et al. | 606/7 |
| 6,254,597 B1 | * | 7/2001 | Rizoiu et al. | 606/7 |
| 6,315,756 B1 | * | 11/2001 | Tankovich | 604/35 |
| 6,350,261 B1 | * | 2/2002 | Domankevitz et al. | 606/9 |
| 6,443,978 B1 | * | 9/2002 | Zharov | 606/2 |
| 6,464,694 B1 | * | 10/2002 | Massengill | 606/2 |

* cited by examiner

Primary Examiner—Roy D. Gibson
Assistant Examiner—Henry M Johnson, III
(74) Attorney, Agent, or Firm—Etherton Law Group, LLC; Sandra L. Etherton

(57) ABSTRACT

A lipoplasty method which includes applying laser energy to the adipose tissue externally through the skin at the same time suction is applied to the targeted tissue. The preferred method includes introducing a solution through an opening in the body to cause the solution to come into contact with adipocytes in the adipose tissue before or simultaneous with applying the laser energy. Optionally, the method can further include reducing inflammation by applying laser energy externally through the skin. Also optionally, the method can include reducing pain by applying laser energy externally through the skin.

10 Claims, 2 Drawing Sheets

METHOD FOR PERFORMING LIPOPLASTY USING EXTERNAL LASER RADIATION

CROSS-REFERENCE TO RELATED APPLICATIONS

This application claims the benefit of U.S. Provisional Application No. 60/273,282 filed Mar. 2, 2001 now abandoned.

FIELD OF INVENTION

This invention relates generally to the use of lasers in surgical procedures. More particularly, it relates to a method for performing lipoplasty by exposing adipose tissue to laser radiation to facilitate its removal from the body.

BACKGROUND

There is a great demand for the cosmetic surgical procedure known as liposuction, wherein excess adipose tissue, also known as fat, is vacuumed from the body of a patient. The typical purpose of the liposuction procedure is to leave the patient thinner, with aesthetically more appealing body contours. For example, liposuction is often performed on patients to remove excess fat in the abdominal, buttock, thigh, breast and arm regions of the body.

Adipose tissue is made of adipocytes, or fat cells, which are enclosed membranes filled with globules of triglycerides. In normal fat the fat cells have regular contours and form into grapelike clusters. The intracellular fat is relatively fluid and, if the membrane is pierced, will flow out of the cell into the interstitial space. The interstitial space includes nerves, blood vessels, and collagenic fibers, among other substances.

Liposuction is performed by inserting a narrow tube, or cannula, through a tiny incision in the skin into the subcutaneous fatty tissue. The cannula is repeatedly pushed then pulled through the fat layer, separating and puncturing the fat cells and suctioning them out. Suction action through the cannula is provided by a vacuum pump or a large syringe.

In contrast to the aesthetic improvements to the body made possible by liposuction, the procedure does carry with it some risks and side effects. Due to the physical damage induced, the procedure can damage nerves and vasculature in the surrounding area, often resulting in significant loss of blood as the blood is vacuumed out with the fat. In addition, the post-procedure recovery period is often accompanied by a great deal of inflammation, bruising and concomitant pain.

Since the liposuction technique was first developed there have been many improvements to the technique, with the goal of making the surgery less dangerous for the patient, as well as reducing the negative aspects of the post-operative recovery period. For example, in the tumescent technique known in prior art, a saline solution containing very dilute amounts of at least an anesthetic and a vasoconstrictor is injected subcutaneously into the area to be suctioned. The anesthetic reduces operative and post-operative pain and the vasoconstrictor helps reduce blood loss. The added fluid forms an emulsion with the fat cells, which has a lower viscosity than the fat cells alone and is therefore easier to suction. The result is increased rate and completeness of fat removal, decreased blood loss, decreased post-operative bruising and improved recovery time.

Cannulas have been improved by enabling the cannula to emit laser light and ultrasound energy directly onto the fat cells. This internal application of energy melts the cell wall, releasing the intracellular fat, thereby making the fatty tissue less viscous and more easily suctioned up through the narrow cannula. These procedures suffer the disadvantage of still having to physically stab the cannula repeatedly in the fat layer as well as essentially melting the adipose tissue, resulting in undesirable levels of bruising, inflammation, pain and blood loss.

Electromagnetic energy, such as microwave, ultrasound or radio frequency radiation, has also been used to improve the procedure by reducing the size of fat cells. An intumescing solution is again injected below the skin and electromagnetic energy is applied externally to the body. The electromagnetic energy heats the fatty tissue and increases fat lipolysis. These procedures are disadvantageous in that they utilize such high energy sources that they excessively heat the surrounding tissue, which can result in damage to the tissue and pain.

Over the past decade, low energy laser therapy (LLLT) has been used increasingly in the treatment of a broad range of conditions such as treatment and repair of injured muscles and tendons. LLLT has improved wound healing, reduced edema, and relieved pain of various etiologies. LLLT has been used successfully post-operative to liposuction to reduce inflammation and pain.

It is desirable to remove fat with less damage to the fatty tissue, less blood loss, less post-operative bruising, inflammation, and pain than what existing methods enable. Therefore, an object of this invention is to provide an improved method of liposuction which facilitates removal of fat with limited physical damage to the surrounding tissue and structures. It is another object of this invention to provide an improved method of liposuction which reduces blood loss. It is another object of this invention to provide an improved method of liposuction which reduces post-operative inflammation and post-operative pain.

SUMMARY OF THE INVENTION

This invention is an improved lipoplasty method which includes applying laser energy to the adipose tissue externally through the skin at the same time suction is applied to the targeted tissue. The presently preferred method includes introducing a solution through an opening in the body to cause the solution to come into contact with adipocytes in the adipose tissue before or simultaneous with applying the laser energy. Optionally, the method can further include reducing inflammation by applying laser energy externally through the skin. Also optionally, the method can include reducing pain by applying laser energy externally through the skin.

DETAILED DESCRIPTION OF THE INVENTION

Figure 1:
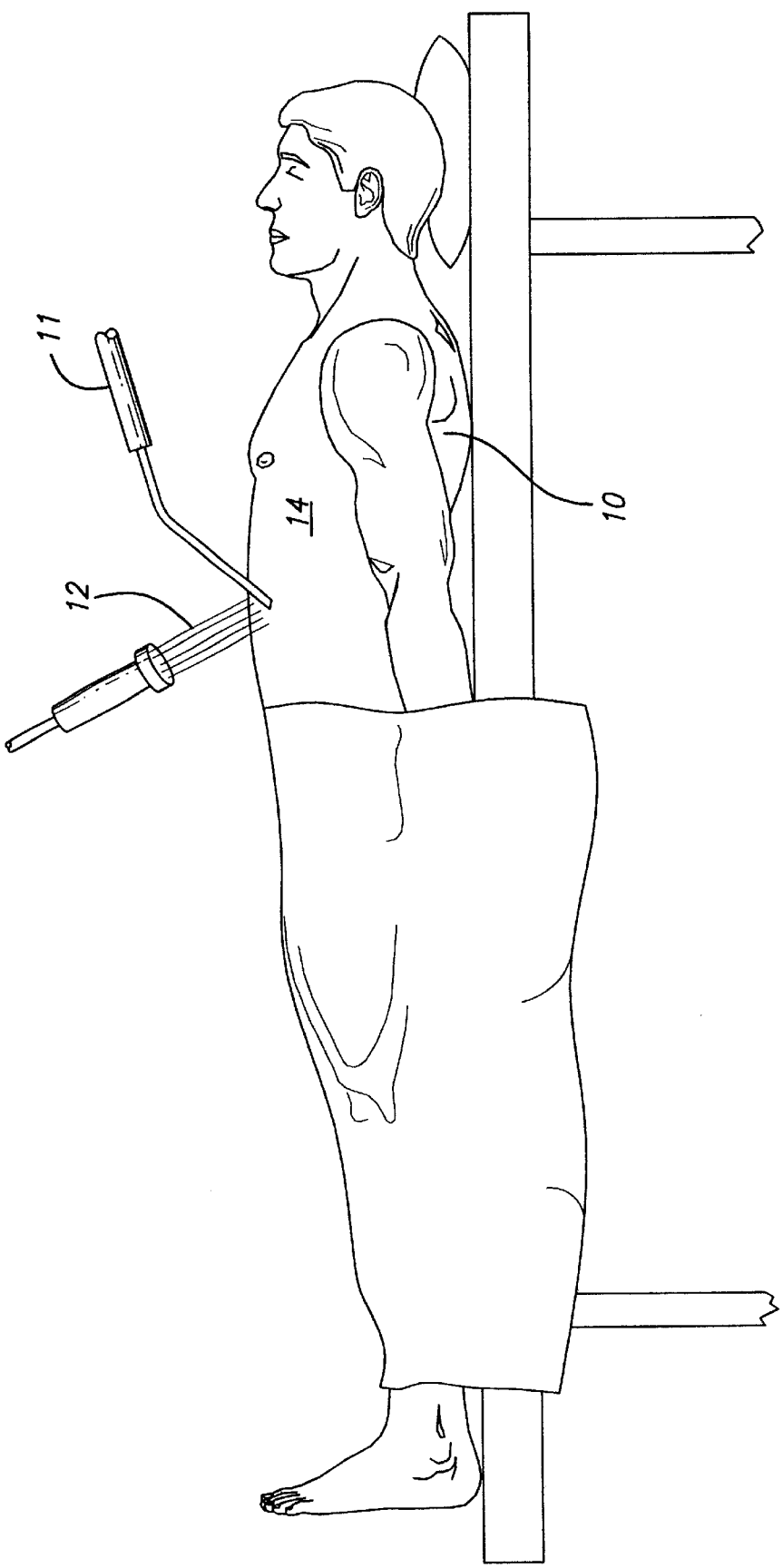
FIG. 1 Schematic illustration of application of low-level laser radiation.

This invention is a method for removing adipose tissue from a patient's body 10. As illustrated in FIG. 1, a cannula 11 is inserted through a tiny incision in the skin 14 into the adipose tissue that is desired to be removed. As is known in the art, a vacuum pump or a large syringe is attached to the cannula 11 to provide suction (not shown). Laser energy 12 is applied to the adipocyte tissue externally through the skin 14 of the patient while applying suction with the cannula 11. Sufficient laser energy is applied during the suctioning to release at least a portion of the intracellular fat into the interstitial space. The adipose tissue, including at least the released intracellular fat, is suctioned out of the body through the cannula 11. Other substances in the interstitial space may also be suctioned out along with the released intracellular fat. The procedure may be repeated in one or more additional areas to remove additional fat there. In that event, additional laser energy would be applied externally to the new area during suction and the fat would be vacuumed out through the cannula 11.

To further facilitate removal of adipocytes, a solution is introduced to the adipose tissue to be treated through an opening in the body, preferably by injection. The solution contains saline and dilute amounts of at least an anesthetic such as lidocaine and a vasoconstrictor such as adrenaline. The solution may also contain a reduction agent such as sodium bicarbonate. The solution is placed into contact with the adipose tissue before or simultaneous with applying the laser energy.

Figure 2:
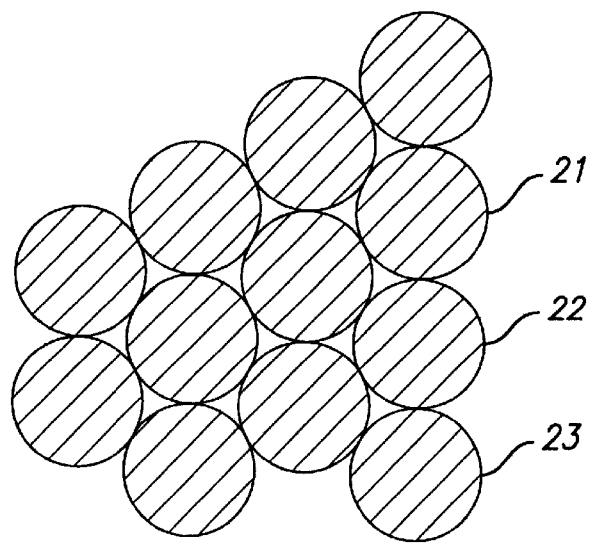
FIG. 2 Schematic illustration of normal fat cells.
Figure 3:
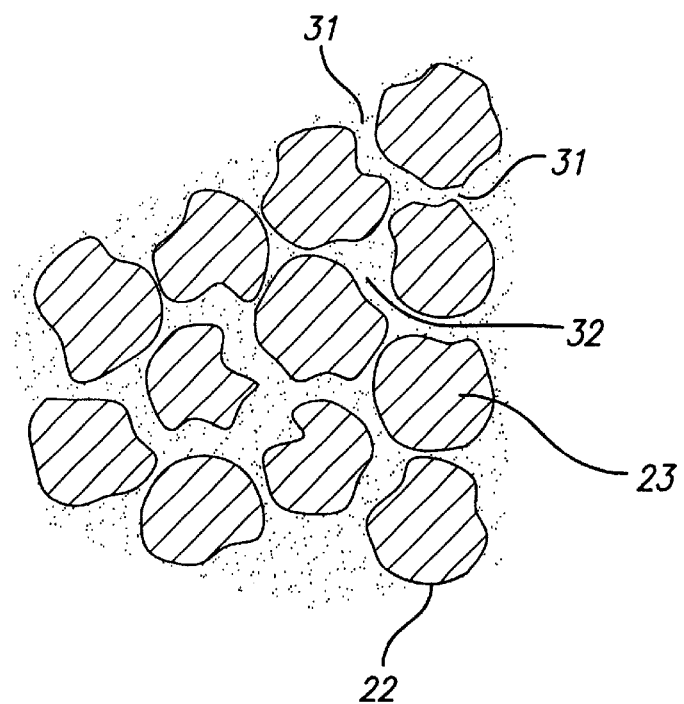
FIG. 3 Schematic illustration of fat cells after externally-applied low-level laser radiation.

The mechanism involved in releasing the intracellular fat from the cells is believed to be the formation of a transitory pore in the cell membrane. FIG. 2 illustrates adipose tissue comprising normal fat cells 21 wherein the cell membrane 22 is filled with intracellular fat 23. As explained in *Stimulatory Effect of 635 nm Low Level Laser Energy on Adipose Tissue: Mechanism for Fat Liquidation* by Neira, MD, et al., incorporated here by reference, scanning electron microscopy (SEM) and transmission electron microscopy (TEM) analysis of irradiated cells shows disrupted cell membranes upon sufficient doses of low-level laser energy. See FIG. 3, which illustrates pores 31 in the cellular membrane 22 which have released intracellular fat 23 into the interstitial space 32. Upon cessation of the energy application, the pores 31 close and the cell membrane returns to contiguity and substantially its former shape.

The laser energy applied is low level, that is, the treatment has a dose rate that causes no immediate detectable temperature rise of the treated tissue and no macroscopically visible changes in tissue structure. Consequently, the treated and surrounding tissue is not heated and is not damaged. Preferably the laser light is visible to the human eye so that the area of application is easily determined. A laser device that provides this low-level energy is known in the art as a cold laser, such as the invention described in U.S. Pat. No. 6,013,096 issued to one of the inventors and incorporated herein by reference. Other lasers known in the art for use in low-level laser therapy include Helium-Neon lasers having a 632 nm wavelength and semiconductor diode lasers with a broad range of wavelengths between 600–800 nm.

The dosage of laser energy required to achieve release of the intracellular fat into the interstitial space will vary depending on the thickness of the patient's skin, thickness of fatty tissue, and other biological factors peculiar to each patient. The following example is illustrative:

EXAMPLE 1

A 635 nm laser (emitting a visible red light) with maximum power of 10 mW was used in combination with the tumescent technique. At 4 minutes of radiation applied, equating to 2.4 joules of energy, fat cell membranes were destroyed in 80% of the cells present, facilitating the release of intracellular fat. At 6 minutes of radiation applied, equating to 3.6 joules of energy, fat cell membranes were destroyed in 99.8% of the cells present, facilitating the release of intracellular fat.

Optionally, the method can further include reducing inflammation by applying laser energy externally through the skin, before, during or after the suction. Also optionally, the method can include reducing pain by applying laser energy externally through the skin, before, during or after the suction. Different therapy regimens require diodes of different wattages. The preferred laser diodes use less than one watt of power each to simultaneously facilitate liposuction, treat post-operative inflammation, and post-operative pain. Diodes of various other wattages may also be employed to achieve the desired laser energy for the given regimen.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A method for removing adipose tissue containing fat cells having intracellular fat and interstices between the fat cells from the body of a patient, the method comprising:
   a) applying laser energy to the adipose tissue externally through the skin of the patient with a laser device that does not touch the patient in order to release at least a portion of the intracellular fat into the interstices of the fat cells; and
   b) applying suction to the adipose tissue to remove it from the body.

2. The method of claim 1, further comprising introducing a solution through an opening in the body to cause the solution to come into contact with fat cells in the adipose tissue before or simultaneous with applying the laser energy.

3. The method according to claim 2 wherein the solution contains at least an anesthetic.

4. The method according to claim 2 wherein the solution contains at least a vasoconstrictor.

5. The method according to claim 1 wherein the laser energy is provided by a laser device having power of less than 1 watt.

6. A method for removing adipose tissue from the body of a patient comprising:
   a) applying laser energy to the adipocyte tissue externally through the skin of the patient with a laser device that does not touch the patient in order to liquefy at least a portion of the adipose tissue; and
   b) applying suction to the liquefied adipose tissue to remove it from the body.

7. The method of claim 6, further comprising introducing a solution through an opening in the body to cause the solution to come into contact with adipocytes in the adipose tissue before or simultaneous with applying the laser energy.

8. The method according to claim 7 wherein the solution contains at least an anesthetic.

9. The method according to claim 7 wherein the solution contains at least a vasoconstrictor.

10. The method according to claim 6 wherein the laser energy is provided by a laser device having power of less than 1 watt.

* * * * *